United States Patent [19]

Fabricius et al.

[11] 4,388,309

[45] Jun. 14, 1983

[54] PROCESS FOR SUPPRESSING GRAFT REJECTION IN ORGAN TRANSPLANTATION

[75] Inventors: Hans-Åke Fàbricius, Breisach; Eckart U. Köttgen, Freiburg, both of Fed. Rep. of Germany

[73] Assignee: Shanksville Corporation, N.V., Netherlands Antilles

[21] Appl. No.: 272,130

[22] Filed: Jun. 10, 1981

[51] Int. Cl.³ .............................................. A61K 31/70
[52] U.S. Cl. .................................... 424/180; 128/1 R
[58] Field of Search ................. 424/180; 536/116, 119; 128/1 R

[56]  References Cited

PUBLICATIONS

Kasai et al., Nature, vol. 291, pp. 334-335, May 1981.
Kasai et al., Eur. J. Immunol., vol. 10, pp. 175-180, 1980.
Ryan and Shinitzky, Eur. J. Immunol., vol. 9, pp. 171-175, 1979.
Whisler and Yates, J. Immunol, vol. 125, No. 5, pp. 2106-2111, 1980.
Lengle et al., Biol. Abs. 68-035938, 1979.

Primary Examiner—Allan Lieberman
Assistant Examiner—Patricia Short
Attorney, Agent, or Firm—Sherman & Shalloway

[57]  ABSTRACT

Suppression of the immunological rejection mechanism of a host which has received an organ transplant in achieved by the daily administration to the host of a ganglioside agent which effectively blocks the soluble immunological cell mediator interleukin 2 and /or a blastogenic factor. By binding to the mediator for T cell blast formation the mediator is prevented from binding to the asialo GM1 receptor on the surface of the T effector cell. Blastogenesis does not occur and the cell mediated rejection of the graft is prevented.

8 Claims, No Drawings

PROCESS FOR SUPPRESSING GRAFT REJECTION IN ORGAN TRANSPLANTATION

This invention relates to the suppression of the cell mediated host versus graft rejection mechanism in transplantation of organs from a donor to a recipient (host). More particularly, this invention relates to the use of chemical blocking agents which interfere with the ability of the host's cellular immune system to attack a foreign graft organ.

It is well known that a graft from a genetically dissimilar member of the same species (allogeneic graft) can generate a population of killer T cells which are specifically cytotoxic for graft target cells bearing the major histocompatibility (MHC) antigens of the donor. The mechanism for the generation of these cytotoxic T cells (CTC) involves a complex series of reactions on the cellular level which is believed to be initiated by the presentation to, and recognition by, the host's macrophage cells, of the transplantation antigens on the donor graft. The macrophage cells respond by synthesis and release of a first signal (interleukin 1; IL-1). The interleukin 1, in turn, together with a comitogenic blood serum glycoprotein (PHILIP, see applicants' corresponding application, Ser. No. 255,251, filed Apr. 17, 1981, incorporated herein by reference) activates a particular subpopulation of accessory cells, generally believed to be T helper cells, for production of a second signal (interleukin 2; IL-2; also known as T cell growth factor; TCGF).

It is the second signal which acts on the subpopulation of T cells known as T effector cells to effect T cell growth. The T cell blasts are the cytotoxic T cells or killer T cells which specifically recognize the graft cells and effect the graft rejection process.

It has recently been reported in the literature that asialo GM1, which is a glycosphingolipid, is a surface component densely expressed on mouse NK (natural killer) cells and further that the natural killing function of the NK cells—which are closely related to cytotoxic T cells and perhaps the NK cells themselves are destroyed by anti-asialo GM1 antibodies [Masataka Kasai & al.: "A glycolipid on the surface of mouse natural killer cells", Eur.J.Immunol., Vol. 10, pages 175–180 (1980) and Masataka Kasai & al.: "In vivo effect of anti-asialo GM1 antibody on natural killer activity", Nature, Vol 291, pages 334–335 (May 28, 1981)].

This finding comfirms the experimental results and hypotheses of the present inventors that desialo GM1 is the surface receptor on human T effector cells which directly recieves the second signal from interleukin 2 or perhaps from a "blastogenic factor" which in turn causes the modification of the surface receptor to a form which can react with IL-2 or still alternatively which causes the expression on the T effector cell of a new surface receptor which can react with IL-2.

By whichever of these mechanisms the T effector cells are transformed to cytotoxic T cells the present invention has been completed on the basis of the finding that incorporating desialo GM1 or similar gangliosides in in vitro T cell culture systems containing IL-2 prevents proliferation of T cell blasts in growing T cell lines and/or prevents transformation of T effector cells to T cell blasts. This observation therefore leads to an in vivo procedure for modification of the cell mediated immunological graft rejection mechanism by blocking the formation of cytotoxic T cells at the level of the T effector cells and without destroying macrophage cells. Accordingly, the procedure of the present invention is highly advantageous as compared to presently available techniques for transplant protection, particularly by the use of immunosuppressive drugs. Since immunosuppressive drugs such as cortisone derivatives function by killing the macrophage cells they also inhibit other immunological reactions of the host such as the humoral antibody system. Therefore such drugs will subject the patient to increased risk of infectious diseases. In addition, since conventional immunosuppressive therapy usually starts at dosage levels which do not entirely kill off the macrophage cells there will be some production of IL-1 and IL-2 and resulting T cell blast formation. At the time of the graft transplantation therefore the consequence of IL-2 and T cell blasts will allow the latter to proliferate until the Il-2 is consumed. This process generally requires several days. In contrast, the immunosuppressive blocking agents of this invention require less than 24 hours to effectively terminate cytotoxic T cell proliferation and to kill off any existing cytotoxic T cells.

Other common immunosuppressive drugs such as azathioprine and methotrexate are used because of their toxicity to dividing cells and therefore pose the danger of toxicity for cells of the bone marrow and also of the small intestine. Such defect is not present with the ganglioside blocking agents of this invention.

Accordingly, it can be seen that the present invention provides an effective method for immunosuppressive therapy in allogeneic graft transplantation operations by blocking soluble mediators which may be either or both of a blastogenic factor or interleukin 2 to thereby prevent proliferation of existing cytotoxic T cells and natural killer cells and to also prevent occurrence of blastogenesis of T effector cells to cytotoxic T cell blasts using gangliosides and ganglioside derivatives as the blocking agent.

DETAILED DESCRIPTION OF THE INVENTION

The transplantation of organ grafts such as kidney, heart, liver, pancreatic islets, bone marrow and the like, even when donor and recipient are carefully tissue type matched, inevitably involves the host versus graft (and, in the case of bone marrow transplantation, graft versus host) immunological cell mediated rejection mechanism. The rejection mechanism actually involves several potential pathways, [see for example "Essential immunology", 3rd Edition by Ivan Roitt, Blackwell Scientific Publications (1977), pages 234–239], but the direct killing by sensitized T cells, i.e. cytotoxic T cells is clearly the most important.

Under normal circumstances T effector cells are circulating in the blood system. When an organ is transplanted in the host, the host's macrophage cells coming into contact with the graft recognize it as foreign and after a few days become sensitized. This sensitization results in the production by the macrophages of interleukin 1 which in turn, with the comitogenic factor PHILIP induces cellular production of interleukin 2. IL-2 and probably also a blastogenic factor which is itself synthesized by either the sensitized macrophage cells or by an accessory cell, probably a T cell, activate resting T effector cells to form T cell blasts i.e. cytotoxic T cells. If nothing is done to prevent the formation of the cytotoxic T cells they will attack and kill the graft cells until the entire graft is destroyed.

Therefore, to prevent the T effector cells from undergoing blastogenesis to their activated natural killing form the T effector cell must somehow be prevented from recieving the signal from Il-2 and/or the blastogenic factor. Since it is known that the relevant surface receptor on the T effector cell is desialo GM1 either or both of the IL-2 or blastogenic factor must be capable of reacting with this ganglioside.

Accordingly, by introducing sufficient quantity of desialo GM1 or structurally similar ganglioside to the host all or nearly all of the soluble mediators which would otherwise react with the desialo GM1 surface receptor will instead react with the introduced desialo GM1 blocking agent. The blastogenic signal is thereby prevented from activating the T effector cell and no blast transformation takes place.

Other blocking agents which can be used, in addition to desialo GMl include other desialylated gangliosides such as desialo GD and its subgroups, especially GD 1a and GD 1b and GT and its subgroups, especially GT 1.

Desialo (or asialo) GMl has the formula Gal←(betal-3)←GalNac←(betal-4)←Glc←(betal-1)←Cer. The formula of the gangliosides GD 1a and 1b and GT 1 are described on page 106 in "Cell surface carbohydrate chemistry" edited by R. E. Harmon, Academic Press Inc. (1978), chapter by L. D. Kohn & al. The definition of these abbreviations are provided, for example, in "The Nomenclature of lipids", Eur.J.Biochem. 79, 11 (1977). Desialo GMl and the other useful ganglioside blocking agents are commercially available in highly purified form.

The gangliosides are characterized by the presence of a portion which is soluble in organic solvents and a portion which is soluble in aqueous solvents. Accordingly, the gangliosides can be dissolved in an aqueous-/organic solvent mixture or coupled to water soluble organic carriers. Suitable organic carriers would include, for example, albumin, antibodies, lectins, glycoproteins, Desoxyribonucleic acid, dextrans and liposomes. Techniques for the use of these organic carriers can be found in "Drug Carriers in Biology and Medicine" edited by G. Gregoriadis, Academic Press, (1979). Suitable organic solvent would include for example alcohol and Dimethylsulfoxide. Organic solvent to water ratios from about 0:100 to about 1:100 can be used.

The ganglioside blocking agent is administered to the patient in an amount which is sufficient to react with the soluble mediators of the T cell blast transformation which would be available for reaction with the desialo GMl surface receptors. Generally, amounts of blocking agent in the range from about 0.5 ug to 10 mg per kilogram of body weight per day will be sufficient to effectively suppress T cell blastogenesis and T cell proliferation.

The effective daily dosage can be administered as a single injection or as two or more injections. However, since it is most probable that the ganglioside is reacting with interleukin 2 a single daily application should be sufficient because about a 24 hour period is required for maximal production of IL-2.

Each injection can be administered intravenously. However, it is also within the scope of the invention to provide the ganglioside blocking agent in an oral dosage form which will allow the ganglioside to be absorbed intact into the blood system in the prescribed amounts. In order to minimize the risk of infections after the operation, it seems convenient not to start the treatment with the blocking agent until about two days after the patient has received the graft. It is well established that the rejection mechanism will not be activated until at least two days after the operation.

The method of this invention can be used whenever it is necessary to prevent rejection of a graft of an organ from a donar to a host for any degree of relationship, i.e. siblings; parent-child; tissue typed but unrelated, etc. In general the principal applications presently contemplated include heart, kidney, liver, pancreatic islets, and bone marrow transplantants.

The present invention is further illustrated by the following non-limiting examples:

EXAMPLE 1

The following test is conducted to determine the inhibition of tumor cell killing capability of cytotoxic T cells activated by interleukin 2:

Tumor cells from HeLa strain are labelled with radioactive chromium. The cells are washed and divided into two portions comprising the same cell number. Both portions are coincubated with cytotoxic T lymphoblasts for 18 hours. The culture medium contains IL-2. To one of the portions, at the beginning of the cocultivation, desialo GMl is added in a concentration of 2 micrograms per ml of culture medium. The culture medium is decanted and the cells are pelleted in a centrifuge. The release of chromium from the labelled tumor cells indicates that the cells have been killed. The results are summarized in table 1.

TABLE 1

| | % of Cr released | | |
|---|---|---|---|
| | Target and T cell | Target and control | Target and IL-2 |
| without asialoGM1 | 85.1 | 4.1 | 0.1 |
| with asialoGM1 | 5.3 | 3.8 | — |

EXAMPLE 2

This example illustrates that asialo GMl reacts with a soluble mediator for T lymphocyte blastogenesis inhibiting cytotoxic T cell formation.

Peripheral blood lymphocytes are isolated by a density gradient centrifugation on ficoll hypaque and incubated 24 hours in the absence of serum proteins.

Interleukin 2 containing tissue culture medium RPMI 1640 is treated with asialo GMl in a concentration of 5 micrograms per ml of culture medium. The incubation with asialo GMl is performed at 37° C. for 30 minutes. Thereafter the treated culture medium is dialysed against RPMI 1640 without supplements for 24 hours at a temperature of 4° C. The cells are incubated in the dialysed (and thus containing no free asialo GMl) culture medium for 7 days. For dialysis, the critical micellar concentration (CMC) of the ganglioside has to be regarded. If it is exceeded, dialysis will be impossible. CMC values for each ganglioside have been established, and are readily available. In contrast to the situation in controls, not treated with asialo GMl, no blast transformation of T cells is observed.

What we claim is:

1. A method for inhibiting cell mediated rejection of organ transplants from a donor to a host comprising administering to the host an immunologically suppressive effective amount of from about 0.5 $\mu g$ to about 10 mg per kilogram body weight per day of a desialylated ganglioside capable of blocking soluble mediators needed for T cell blast formation and proliferation.

2. The method of claim 1 wherein the desialylated ganglioside is asialo GM1.

3. The method of claim 1 wherein the desialylated ganglioside is asialo GD 1a, GD 1b or GT 1.

4. The method of claim 1 wherein the organ transplant is a heart transplant, kidney transplant, liver transplant, pancreatic islet transplant or a bone marrow transplant.

5. The method of claim 1 wherein the ganglioside is administered to the host once or twice daily as an injectable solution of the ganglioside in an alcohol/water mixture having a ratio of alcohol to water of 0:100 to 1:100.

6. The method of claim 4 wherein the injectable solution comprises an aqueous solution of a complex of the ganglioside with a water soluble organic carrier.

7. The method of claim 5 wherein the organic carrier is selected from the group consisting of albumin, antibodies, lectins, glycoproteins, desoxyribonucleic acid, dextran and liposomes.

8. The method of claim 1 wherein the ganglioside is administered to the host starting during a period of from 0 to 48 hours after the host recieves the organ transplant.

* * * * *